(12) United States Patent
Welch (10) Patent No.: US 11,185,403 B2
(45) Date of Patent: Nov. 30, 2021

(54) ENDOLUMINAL PROSTHESIS ASSEMBLY

(75) Inventor: Jonathan B. Welch, Greencastle, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2148 days.

(21) Appl. No.: 13/597,538

(22) Filed: Aug. 29, 2012

(65) Prior Publication Data
US 2013/0053944 A1 Feb. 28, 2013

Related U.S. Application Data

(60) Provisional application No. 61/529,597, filed on Aug. 31, 2011.

(51) Int. Cl.
*A61F 2/07* (2013.01)
*A61F 2/24* (2006.01)
*A61F 2/06* (2013.01)
*A61F 2/89* (2013.01)
*A61F 2/954* (2013.01)

(52) U.S. Cl.
CPC ............. *A61F 2/07* (2013.01); *A61F 2/954* (2013.01); *A61F 2/2418* (2013.01); *A61F 2/89* (2013.01); *A61F 2002/061* (2013.01); *A61F 2002/067* (2013.01); *A61F 2002/075* (2013.01); *A61F 2220/0075* (2013.01)

(58) Field of Classification Search
CPC ...... A61F 2/07; A61F 2/89; A61F 2/95; A61F 2/954; A61F 2/962; A61F 2002/061; A61F 2002/075; A61F 2002/9505; A61F 2002/9511; A61F 2/856; A61F 2/2427; A61F 2/2418; A61F 2002/067
See application file for complete search history.

(56) References Cited

U.S. PATENT DOCUMENTS

| 5,366,473 | A | 11/1994 | Winston et al. |
| 5,667,523 | A | 9/1997 | Bynon et al. |
| 5,916,264 | A | 6/1999 | Von Oepen et al. |
| 6,123,723 | A | 9/2000 | Kónya et al. |
| 6,168,620 | B1 | 1/2001 | Kerr |

(Continued)

FOREIGN PATENT DOCUMENTS

WO  WO 2007/124053  11/2007

OTHER PUBLICATIONS

European Search Report, EP 12275127, search report completed Oct. 30, 2012.

*Primary Examiner* — Majid Jamialahmadi
(74) *Attorney, Agent, or Firm* — Crowell & Moring LLP (57) ABSTRACT

The endoluminal prosthesis assembly comprises a first stent graft having a first end and a second end and an interior lumen. The first stent graft has an expanded position and a compressed position and defines an access port disposed through a wall of the first stent graft between the first and second ends of the first stent graft. The endoluminal prosthesis assembly further comprises a second stent graft being disposed entirely within the interior lumen of the first stent graft. The second stent graft is disposed within the first stent graft and has an expanded position and a compressed position. In the compressed position, the second stent graft contacts only a portion of an interior wall of the first stent graft and the access port is in fluid communication with the interior lumen of the first stent graft.

20 Claims, 8 Drawing Sheets

(56) References Cited

U.S. PATENT DOCUMENTS

| | | | |
|---|---|---|---|
| 6,613,078 B1 | 9/2003 | Barone | |
| 6,695,875 B2 | 2/2004 | Stelter et al. | |
| 6,752,825 B2 | 6/2004 | Eskuri | |
| 7,530,994 B2 | 5/2009 | Thistle | |
| 2002/0013616 A1 | 1/2002 | Carter et al. | |
| 2005/0059923 A1 | 3/2005 | Gamboa | |
| 2005/0113904 A1 | 5/2005 | Shank et al. | |
| 2006/0195172 A1 | 8/2006 | Luo et al. | |
| 2007/0250154 A1* | 10/2007 | Greenberg | A61F 2/07 623/1.13 |
| 2008/0183275 A1 | 7/2008 | Schmid et al. | |
| 2008/0249601 A1 | 10/2008 | Kerr | |
| 2008/0262593 A1 | 10/2008 | Ryan et al. | |
| 2009/0264979 A1 | 10/2009 | Kao et al. | |
| 2010/0137973 A1* | 6/2010 | Sutermeister | A61F 2/856 623/1.15 |

\* cited by examiner

ENDOLUMINAL PROSTHESIS ASSEMBLY

The present application claims priority to U.S. Provisional Patent Application Ser. No. 61/529,597 filed Aug. 31, 2011, the entirety of which is hereby incorporated by reference.

BACKGROUND

This invention relates generally to an endoluminal prosthesis and particularly to a endoluminal prosthesis having a fenestration that is implantable within the human or animal body for the repair of damaged vessels, ducts or other physiological passageways and cavities, and systems and methods for facilitating deployment of such an endoluminal prosthesis.

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or to preserve any remaining vascular integrity by replacing a length of the existing passageway or duct wall that spans the site of failure or defect. Endoluminal prostheses may be of a unitary construction or may be comprised of multiple prosthetic modules.

A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Generally, when deploying an endovascular prosthesis into a body lumen, it is possible to obtain access to such a body lumen from each end of the lumen where necessary, thereby facilitating placement of a device in the lumen. There can be problems, however, if the aneurysm of the aorta extends down into one or other of the iliac arteries. Each of the common iliac arteries branches into the internal and external iliac arteries and it is necessary in such a situation that a blood flow path can be directed through an endovascular stent graft into each of these arteries. The internal iliac artery which extends from the common iliac artery below the aortic bifurcation is for all intents and purposes a blind vessel because there is no practical way of performing an endovascular minimally invasive procedure into that vessel other than by entry from the common iliac artery.

BRIEF SUMMARY

The present embodiments provide an endoluminal prosthesis assembly for placement in a diseased vessel. The endoluminal prosthesis assembly comprises a first stent graft having a first end and a second end and an interior lumen. The first stent graft has an expanded position and a compressed position and defines an access port disposed through a wall of the first stent graft between the first and second ends of the first stent graft. The endoluminal prosthesis assembly further comprises a second stent graft being disposed within the interior lumen of the first stent graft. The second stent graft may be disposed entirely within the interior lumen of the first stent graft. The second stent graft is disposed within the first stent graft and has an expanded position and a compressed position, where the second stent graft is compressed against an interior wall of the first stent graft opposite the access port. In the compressed position, the second stent graft contacts only a portion of an interior wall of the first stent graft and the access port is in fluid communication with the interior lumen of the first stent graft. In the expanded position, the second stent graft engages substantially all of the interior wall of the first stent graft and seals the access port from fluid communication with the interior lumen of the first stent graft.

In one aspect, the second stent graft is secured to the interior wall of the first stent graft. In another aspect, the second stent graft is restrained in the compressed position by a trigger wire arrangement. In another example, the second stent graft is concentric with the first stent graft and has a diameter that is less than the first stent graft when in the expanded position. In another aspect, the length of the second stent graft is shorter than the length of the first stent graft. With the secondary stent graft in the compressed position, the first and second ends of the second stent graft may be restrained and the access port is in fluid communication with the lumen of the primary stent graft, which allows for the deployment of other endoluminal devices through the access port.

In another aspect, a delivery system for an endoluminal prosthesis comprises an introducer that includes a distal end intended to remain outside a patient in use and a proximal end. The proximal end of the introducer has a nose cone dilator and a retention arrangement distal of the nose cone dilator. An endoluminal prosthesis assembly is retained on the introducer. The endoluminal prosthesis assembly comprises a first stent graft having a first end and a second end and an interior lumen. The first stent graft has an expanded position and a compressed position and defines an access port disposed through a wall of the first stent graft between the first and second ends of the first stent graft. The endoluminal prosthesis assembly further comprises a second stent graft being disposed entirely within the interior lumen of the first stent graft. The second stent graft is disposed within the first stent graft and has an expanded position and a compressed position, where the second stent graft is compressed against an interior wall of the first stent graft opposite the access port. The delivery system further includes a trigger wire arrangement engaging a suture arrangement secured to the first end and a suture arrangement secured to the second end of the second stent graft to retain the second stent graft in the compressed position. In one embodiment, the suture arrangement includes a single length of suture material. In another embodiment, the delivery system includes a second suture arrangement secured to the second end of the second stent graft and is engaged with the trigger wire arrangement. In another embodiment, the suture arrangements include a plurality of loops that engage the trigger wire arrangement.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DETAILED DESCRIPTION OF THE DRAWINGS AND THE PRESENTLY PREFERRED EMBODIMENTS

Unless defined otherwise, all technical and scientific terms used herein have the same meaning as commonly understood by one of ordinary skill in the art to which this invention pertains.

The term "prosthesis" means any device for insertion or implantation into, or replacement, for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include, without limitation, blood vessels, respiratory ducts, gastrointestinal ducts, such as the biliary duct, intestines, the esophagus, the pericardial cavity, the thoracic cavity, and the like. Accordingly, the terms "endoluminal device" or "endoluminal prosthesis" describe devices that can be placed inside or moved through any such lumen or duct.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may constitute an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The terms "patient," "subject," and "recipient" as used in this application may refer to any animal, particularly humans.

The terms "proximal" and "distal" will be used to describe opposing axial ends of the delivery system, as well as the axial ends of various component features. The term "proximal" is used to refer to the end of the system (or component thereof) that is initially inserted into the patient, or that is closest to the patient during use. The term "distal" is used to refer to the end of the system (or component thereof) that is closest to the operator during use of the system.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Figure 1:
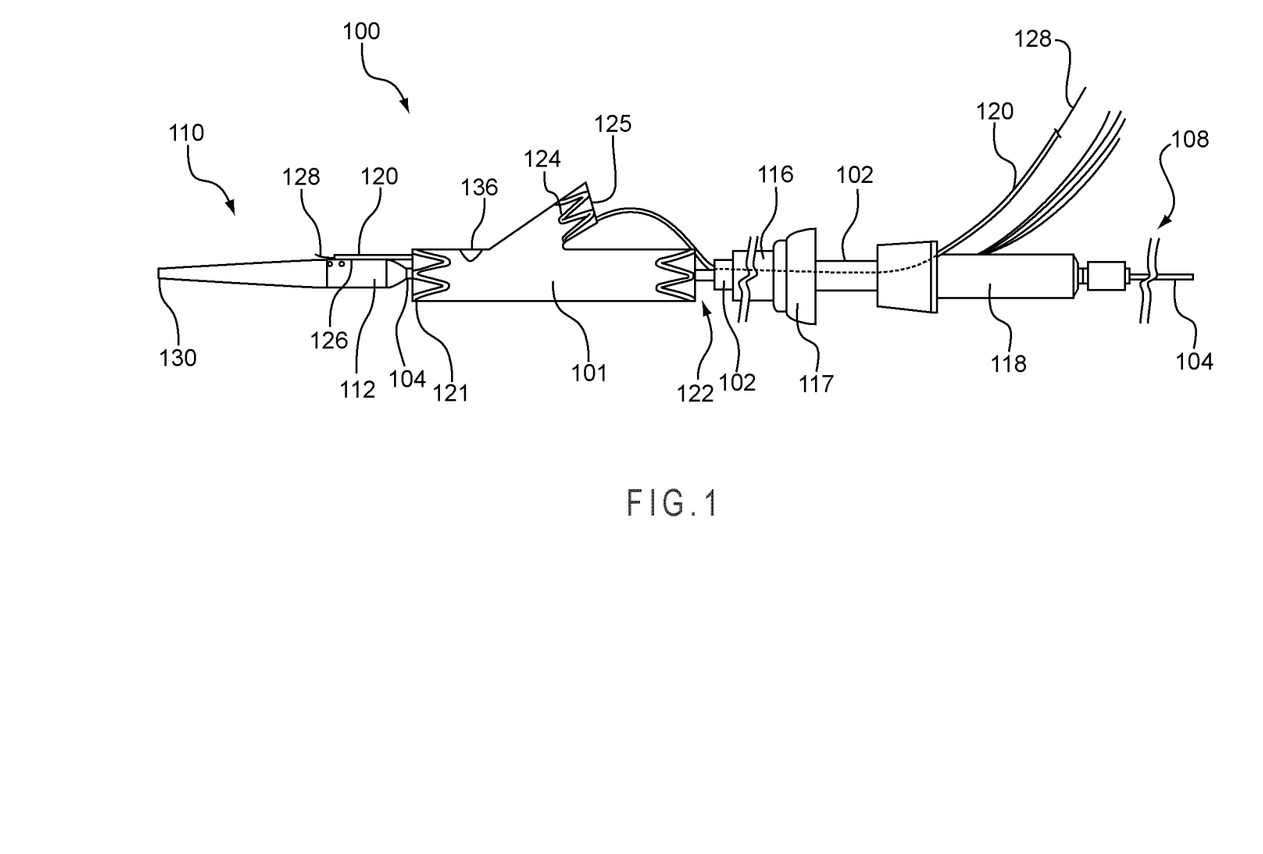
FIG. 1 shows a schematic view of a deployment device for an embodiment of an endoluminal prosthesis assembly.
Figure 2:
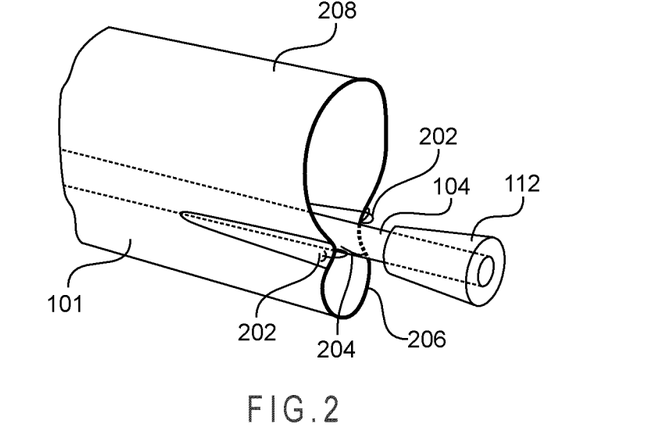
FIG. 2 shows a retention apparatus for retaining the proximal end of the endoluminal prosthesis assembly of FIG. 1.

Now first looking at FIG. 1, an introducer 100 for an embodiment of an endoluminal prosthesis 101 mounted onto the introducer 100 is shown schematically. The introducer 100 has an introducer catheter 102 extending over a guide wire catheter 104. The guide wire catheter 104 extends from the distal end 108 of the introducer 100 to immediately distal of the nose cone dilator 112, which is at the proximal end 110 of the introducer 100. A sheath 116 operated by a sheath manipulator 117 is mounted on the introducer catheter 102. The sheath 116, as illustrated, is withdrawn so that the endoluminal prosthesis 101 is in an expanded position to show detail of the prosthesis 101. The sheath 116 is configured to extend over the endoluminal prosthesis 101 to the nose cone dilator 112 and keeps the endoluminal prosthesis 101 in a compressed configuration prior to deployment within the target vessel. The endoluminal prosthesis 101 is retained at its proximal end 121 by a proximal retention arrangement positioned immediately distal of the nose cone dilator 112. FIG. 2 discloses one method of proximal retention of the endoluminal prosthesis assembly 101. The endoluminal device 101 may be positioned immediately distal of the nose cone dilator 112. As shown, the proximal retention arrangement may comprise loops 202 of fiber or suture material engaged with a trigger wire 204 extending from an aperture in the guide wire catheter 104 distal to the nose cone dilator 112. The loops 202 are placed so that there is formed a smaller 206 and larger 208 fold of the endoluminal prosthesis assembly 101 at its proximal end.

Figure 3:
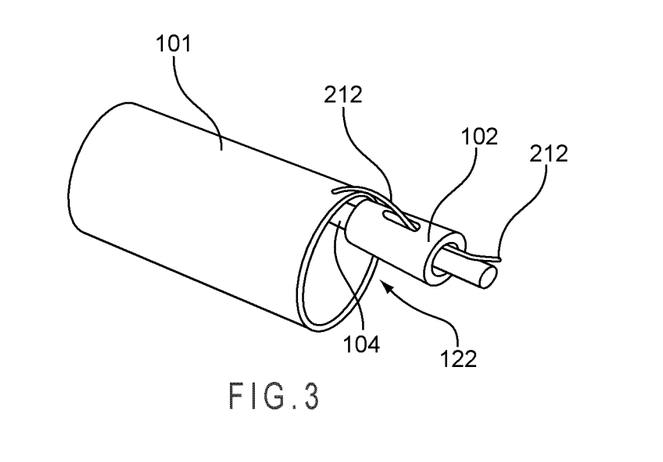
FIG. 3 shows a retention apparatus for retaining the distal end of the endoluminal prosthesis assembly of FIG. 1.

FIG. 3 discloses one method of distal retention of the endoluminal prosthesis assembly 101. As shown, the distal end 122 of the endoluminal prosthesis 101 is retained on the guide wire catheter 104 just proximal of the proximal end of the introducer catheter 102 by means of a loop of trigger wire 212 extending from the introducer catheter 102. Removal of the trigger wire 212 will release the distal end 122 of the endoluminal prosthesis 101.

Referring back to FIG. 1, a handle 118 at the distal end of the introducer catheter 102 enables manipulation of the introducer 100. An indwelling catheter 120 enters a lumen (not shown) of the introducer catheter 102 at the handle 118 and exits from the introducer catheter 102 at the distal end 122 of the endoluminal prosthesis 101. Within the indwelling catheter 120, there is a guide wire 128. This guide wire 128 can be pushed through the indwelling catheter 120 so that it extends beyond the tip 130 of the nose cone dilator 112. Preferably, the proximal end of the indwelling catheter 120 is tapered to closely fit around the guide wire 128 to prevent blood loss through the indwelling catheter 120. The indwelling catheter 120 enters the lumen of the branch 124 through its distal end 125 and exits the endoluminal prosthesis assembly 101 adjacent to the nose cone dilator 112 and extends along the side of the nose cone dilator 112 in a groove 126 formed in the nose cone dilator 112. The endoluminal prosthesis 101 further includes an access port 136.

Figure 4:
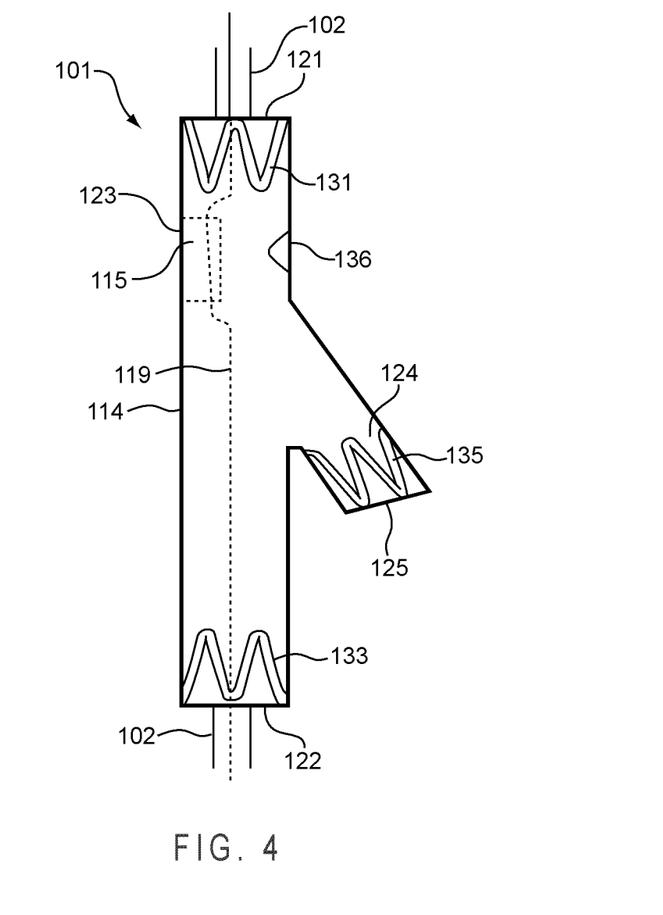
FIG. 4 shows a schematic view of the exterior of the endoluminal prosthesis assembly of FIG. 1.
Figure 5:
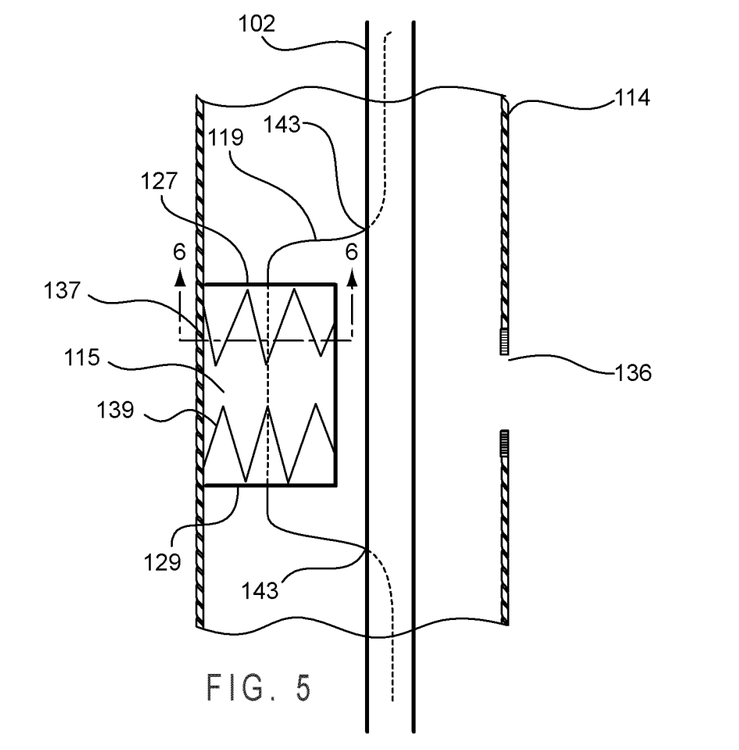
FIG. 5 shows a schematic view of the interior of the endoluminal prosthesis assembly of FIG. 1, where a secondary stent graft is in a compressed position.

FIGS. 4 and 5 provide a more detailed view of the fenestrated endovascular device assembly 101. Referring to FIG. 4, the fenestrated endovascular device assembly 101 includes a stent graft 114 having a substantially tubular main body 123 with a main lumen disposed therethrough and a side lumen through a branch 124. Sealing stents 131, 133 are positioned on the proximal 121 and distal ends 122, respectively, of the main body 123 of the stent graft 114. A sealing stent 135 is positioned on the distal end 125 of the branch 124 of the stent graft 114. The introducer catheter 102 is disposed through the main lumen of the stent graft 114.

The stents 131, 133, 135 may be made from numerous metals and alloys. In one example, the stents 131, 133, 135 comprise a shape-memory material such as a nickel-titanium alloy ("Nitinol"). Moreover, the structure of the stents 131, 133, 135 may be formed in a variety of ways to provide a suitable support structure. For example, one or more stents may be made from a woven wire structure, a laser-cut cannula, individual interconnected rings, or another pattern or design. While one exemplary arrangement is shown in FIG. 4, it will be appreciated that the exact number of stents, and their location, may be varied.

In one example, shown in FIG. 4, the stents 131, 133, 135 may be configured in the form of one or more "Z-stents", each of which may comprise a series of substantially straight segments interconnected by a series of bent segments. The bent segments may comprise acute bends or apices. The stents are arranged in a zigzag configuration in which the straight segments are set at angles relative to each other and are connected by a bent segment. However, as noted above, the stents 131, 133, 135 may comprise any suitable configuration and one or more stents may be provided.

The primary stent graft 114 includes an access port 136, or fenestration, disposed through the wall of the main body 123 and provides access to an internal artery, such as the internal iliac artery. Through the access port 136, additional endoluminal devices, including wire guides, sheathes, and catheters, may be deployed into the internal artery. The primary stent graft 114 also includes a secondary stent graft 115 disposed within its lumen. The secondary stent graft 115 is retained by a trigger wire arrangement 119. The secondary stent graft 115 may be secured to the wall of the primary stent graft 114 by conventional means including, but not limited to, adhesives and sutures.

The primary stent graft 114 and the secondary stent graft 115 may be constructed from a biocompatible material. Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. For example, the primary stent graft 114 and the secondary stent graft 115 may be constructed from woven multifilament polyester, for example and without limitation, Dacron™, produced by DuPont. Dacron™ is known to be sufficiently biologically inert, non-biodegradable, and durable to permit safe insertion inside the human body.

FIG. 5 shows an interior view of an embodiment of the primary stent graft 114. As shown, the secondary stent graft 115 is in a compressed position. The secondary stent graft 115 has a proximal end 127 and a distal end 129. Sealing stents 137, 139 are positioned on the proximal 127 and distal ends 129, respectively, of the secondary stent graft 115. The secondary stent graft 115 is compressed against a portion of the interior wall of the primary stent graft 114 opposite of the access port 136. In alternative embodiments, the secondary stent graft 115 may be placed in other positions within the lumen of the primary stent graft 114. The trigger wire arrangement 119 may include one or more wires which extend from a trigger wire release mechanism (not shown) to the proximal end of introducer 100 distal to the nose cone dilator 112. The trigger wire arrangement 119 is substantially disposed through the introducer catheter 102 and extends from a handle at the distal end of the introducer 100. The trigger wire arrangement 119 may also be disposed through an auxiliary catheter (as described in FIG. 6). Two apertures 143 are disposed through the introducer catheter 102 to provide access to the secondary stent graft 115. The trigger wire arrangement 119 is configured to restrain the proximal 137 and distal ends 139 of the secondary stent graft 115 when the secondary stent graft 115 is in the compressed position. With the secondary stent graft 115 in the compressed position, the access port 136 is in fluid communication with the lumen of the primary stent graft 114, which allows for the deployment of other endoluminal devices through the access port 136. In addition, the secondary stent graft 114 in the compressed position provides unrestricted access to the internal artery through the access port 136 while the secondary stent graft 115 is restrained the compressed position.

Figure 6:
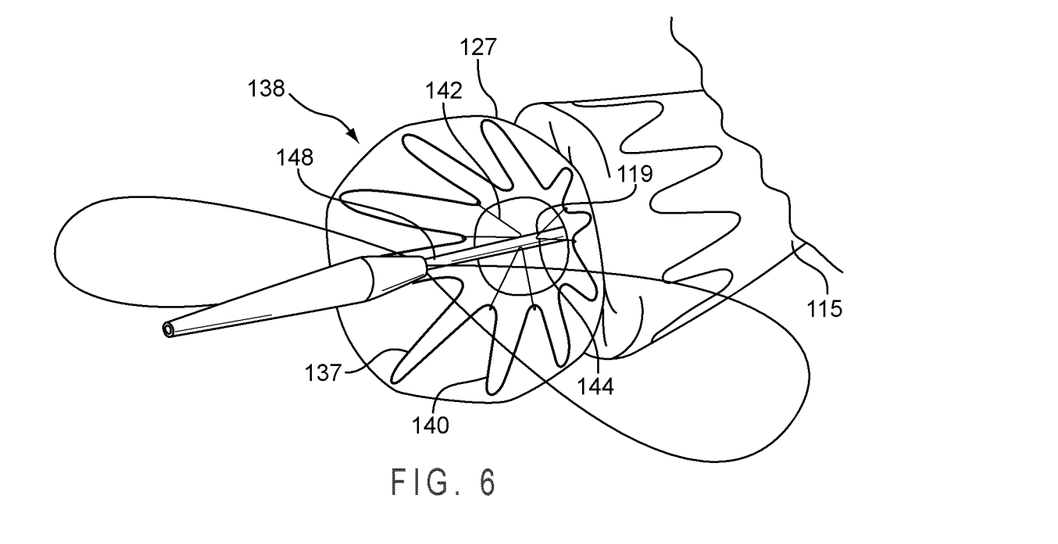
FIG. 6 shows a cross-sectional view of the proximal end of the secondary stent graft of the endoluminal prosthesis assembly of FIG. 1.

An embodiment of the proximal end 127 of the secondary stent graft 115 is shown in greater detail in FIG. 6. As shown, the proximal end 137 of the secondary stent graft 115 may be restrained by the trigger wire arrangement 119 engaging a first suture arrangement 138. The first suture arrangement 138 includes one or more loops 142 that may be pulled into the center of the secondary stent graft 115 towards an auxiliary catheter 148 and held thereto by a trigger wire arrangement 119 within the lumen of the auxiliary catheter 148 through a plurality of openings 144. A plurality of struts 140 of the proximal sealing stent 137 are restrained by each loop 142 of the suture arrangement 138 positioned between bends 141 of the stent 137, thereby pulling the entirety of the proximal end 137 of the stent towards auxiliary catheter 148. The proximal sealing stent 137 may be restrained in such a way that the entirety of the distal end of the proximal sealing stent 137 is pulled inwardly to some extent and thus lies within the circumference of the lumen of the secondary stent graft 115 and holds the secondary stent graft 115 to the auxiliary catheter 148 during deployment. The distal sealing stent 139 of the secondary stent graft 115 can be restrained by a comparable second suture arrangement. In alternative embodiments, the proximal end 137 and distal end 139 may be restrained through the use of other procedures and techniques.

Figure 7:
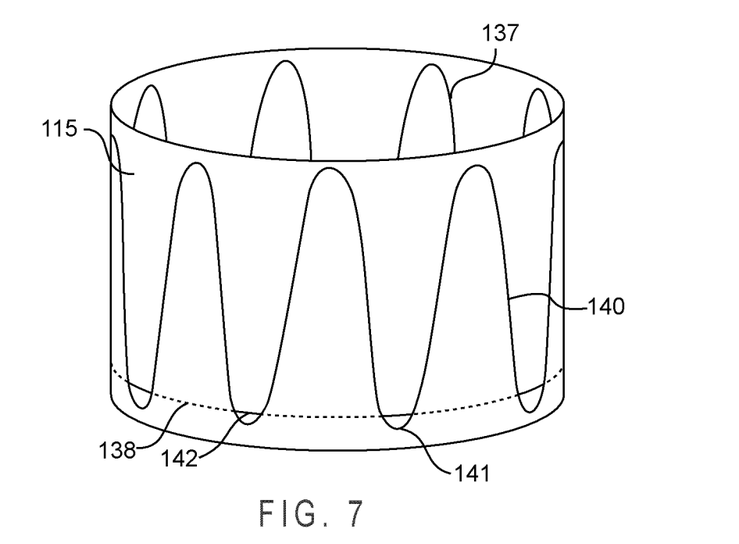
FIG. 7 shows a suture arrangement used for retention of the proximal end of a secondary stent graft of the endoluminal prosthesis assembly of FIG. 1.

A variety of different embodiments of suture arrangements 138 for the secondary stent graft 115 are possible. One embodiment is shown in FIG. 7. FIG. 7 shows the use of a single length of suture material 138 circumscribing the entirety of the circumference of the secondary stent graft 115. Portions of the suture material 138 located on the outside of the secondary stent graft 115 are shown as a dashed line, while portions of suture material 138 on the inside of the secondary stent graft 115 are shown as a thicker solid line. It can be seen that suture material 138 is located on the inside of the secondary stent graft 115 only between the struts 140 of the proximal sealing stent 137, and towards the apices 141 thereof. In this way, the struts 140 act to hide or shield the loops 142 of suture material 138 from any later used medical device. The suture threads 138 are thus somewhat protected by the struts 140 of the proximal sealing stent 137 from snagging on a later inserted medical device. A similar arrangement may also be provided at the proximal end of the proximal sealing stent 137 to restrain this to the auxiliary catheter 148.

The skilled person will appreciate that there are many modifications that could be made to the restraining apparatus of this embodiment. U.S. patent application Ser. No. 12/609,066 entitled "Introducer for Deploying a Stent Graft in a Curved Lumen and Stent Graft Therefor" discloses arrangements for restraining the ends of an endoluminal device and is herein incorporated by reference in its entirety.

Figure 8:
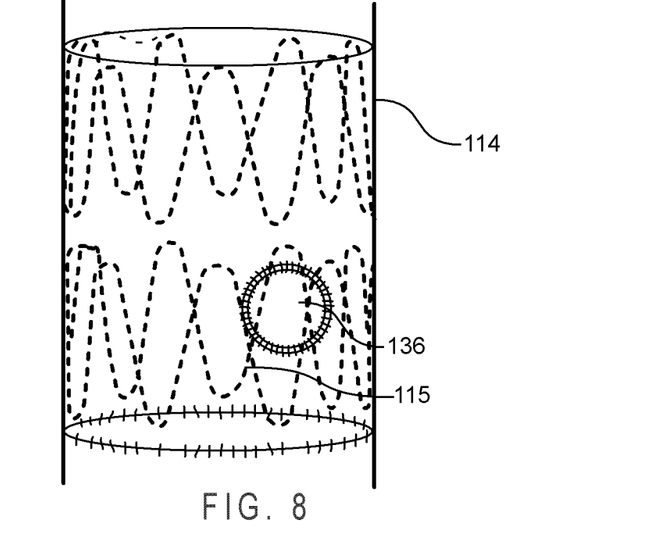
FIG. 8 shows the cross-sectional view of the secondary stent graft of the endoluminal prosthesis assembly of FIG. 1, where the secondary stent graft is in an expanded position.

FIG. 8 discloses an embodiment of the primary stent graft 114 where the secondary stent graft 115 is in the expanded position. In the expanded position, the secondary stent graft 115 engages against the interior wall of the endoluminal prosthesis to effectively seal the access port 136. The secondary stent graft 115 is completely concentric with the primary stent graft 114. The sealing of the access port 136 precludes access to the internal artery and prevents the possibility of leaks into the prosthesis. The secondary stent graft 115 in the expanded position has an expanded diameter that is less than the expanded diameter of the primary stent graft 114 in the expanded position. The secondary stent graft 115 in this embodiment has a length that is shorter than the length of the primary stent graft 114. In alternative embodiments, the secondary stent graft 115 may have a length that is longer that the length of the primary stent graft 114.

In use, the operator deploys a guide wire for the introducer 100 into the femoral artery, via an incision and extended up beyond the aortic bifurcation to the aorta. The introducer 100 is deployed over the guide wire and the introducer 100 is extended up into the aortic bifurcation. The sheath 116 is withdrawn such that the stent graft 114, including the branch 124, is exposed, but retaining the stent graft 114 at both the proximal and distal ends 121, 122 so that the stent graft 114 is not in a fully expanded configuration. The secondary stent graft 115, disposed within the interior of the primary stent graft 114 in the compressed position, is retained by trigger wire arrangement 119. The trigger wire arrangement 119 engages the suture arrangements 138 secured on the proximal 137 and distal ends 139 of the secondary stent graft 115. The operator introduces a catheter into the stent graft 114 through the access port 136. Through the catheter, the operator can introduce additional endoluminal devices, including, but not limited to, a branch stent graft, into an internal artery through the lumen 125 of the branch 124 of the stent graft 114. The operator may introduce additional endoluminal prostheses into the vessel through the access port 136. U.S. patent application Ser. No. 10/962,763 entitled "Introducer for Iliac Side Branch Device" discloses an arrangement for using an indwelling catheter to access an internal iliac artery and is herein incorporated by reference in its entirety. The secondary stent graft 115 in the compressed position provides the operator with access to the access port 136. Following deployment of the additional endoluminal prostheses through the access port 136, the catheter is removed. The operator may remove the trigger wire arrangement 119 restraining the proximal 137 and distal 139 ends of the secondary stent graft 115. The secondary stent graft 115 moves from the compressed position to the expanded position. The secondary stent graft 115 in the expanded position is concentric with the primary stent graft 114, and engages the walls to effectively seal the access port 136. The operator then releases the proximal 121 and distal 122 ends of the primary stent graft 114, and the introducer 100 is removed from the patient.

Figure 9:
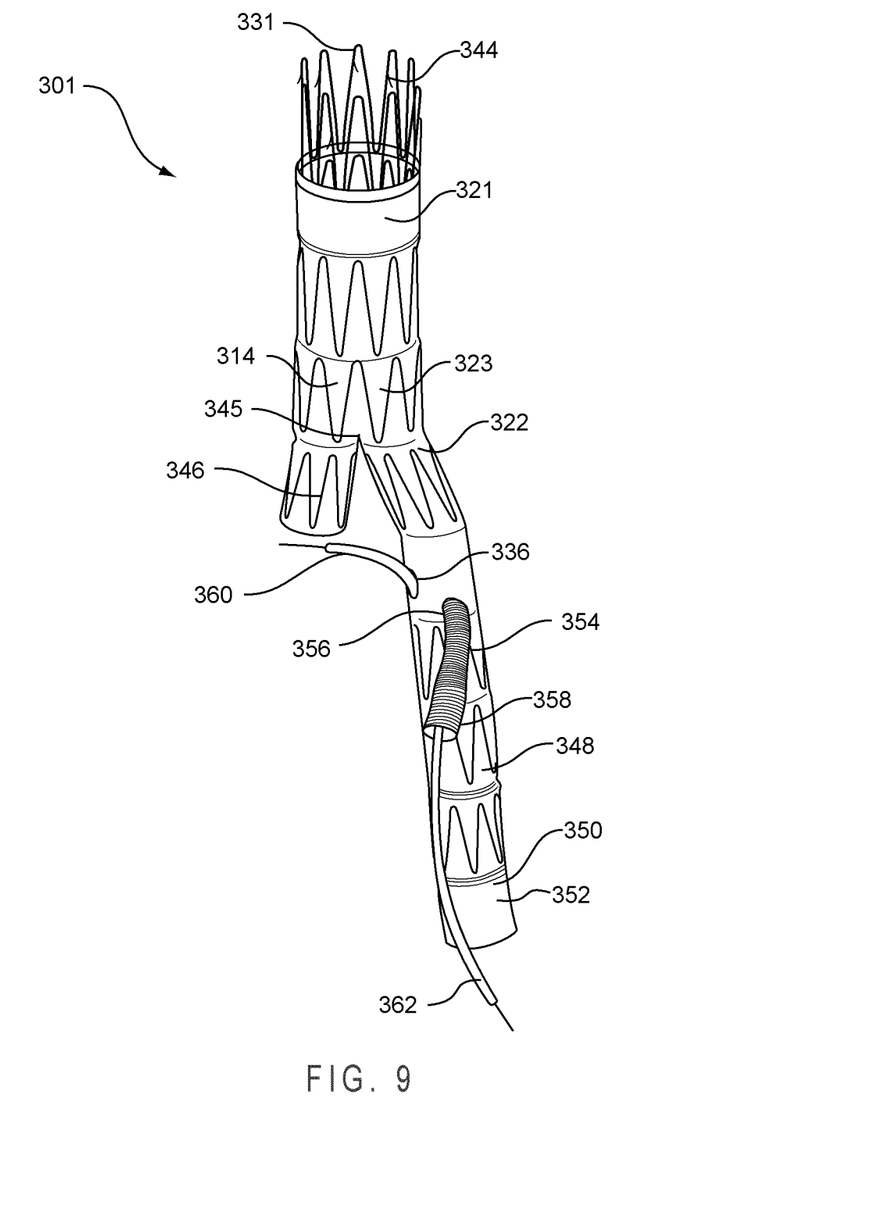
FIG. 9 shows a schematic view of an alternative embodiment of an endoluminal prosthesis assembly.

FIG. 9 provides an alternative embodiment of an endoluminal prosthesis assembly for the treatment of an aortic aneurysm. In this embodiment, the endoluminal prosthesis assembly 301 includes a primary stent graft 314. The primary stent graft 314 has a main body 323 having a proximal end 321 and a distal end 322 having a bifurcation 345. The primary stent graft 314 includes a proximally extending suprarenal stent 331 on its proximal end 321. The suprarenal stent 331 includes barbs 344 configured to engage the wall of the aorta positioned proximal of the renal arteries to secure the primary stent graft 314 when placed within the aorta and to prevent migration within the vessel. The primary stent graft 314 includes a short leg 346 and a long leg 348 extending from the bifurcation 345 of the stent graft 314. The long leg 348 has a sealing surface 350 at its distal end 352. The long leg 348 has a side arm 354 which in this embodiment is in the form of a corrugated tube extending in a partially helical manner from its connection at a fenestration 356 into the long leg 348. The side arm 354 extends in a distal direction and has a distal end 358 remote from its connection with the long leg 348. An access port 336 is disposed within the wall of the long leg 348 proximal of the connection of the side arm 354 into the long leg 348. During deployment of the stent graft 314 into the vasculature of a patient, an in-dwelling catheter 360 extends through the side arm 354 and out through the access port 336. The indwelling catheter 360 includes a guide wire 362.

Figure 10:
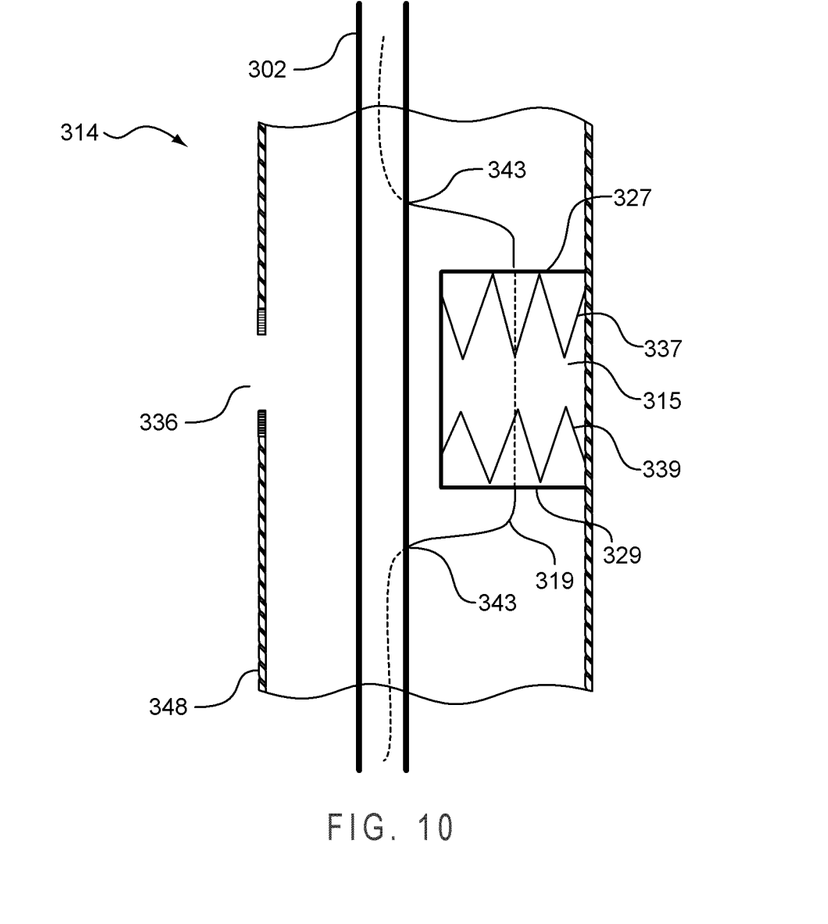
FIG. 10 shows a schematic view of the interior of the endoluminal prosthesis assembly of FIG. 9, where a secondary stent graft is in a compressed position.

FIG. 10 shows the interior of a portion of an embodiment of the long leg 348 of the stent graft 314 while compressed in a delivery device in detail. The delivery device includes an introducer catheter 302, which is disposed through the lumen of the long leg 348. The long leg 348 is substantially tubular having a lumen disposed therethrough. The access port 336 disposed through the wall of the long leg 348 and provides access to an internal artery, such as the internal iliac artery. Through the access port 336, additional endoluminal devices, including wire guides, sheaths, and catheters, may be deployed into the internal artery without interference. The long leg 348 also includes a secondary stent graft 315 positioned within its interior opposite of the access port 336. The secondary stent graft 315 may be secured to the interior wall of the long leg 348 by conventional means including, but not limited to, adhesives and sutures.

As shown, the secondary stent graft 315 is in a compressed position. The secondary stent graft 315 has a proximal end 327 and a distal end 329. Sealing stents 337, 339 are positioned on the proximal 327 and distal ends 329, respectively, of the secondary stent graft 315. A trigger wire arrangement 319 may include one or more which extend from a trigger wire release mechanism (not shown) of a delivery system for an endoluminal prosthesis. The trigger wire arrangement 319 is substantially disposed through the introducer catheter 302. Two apertures 343 are disposed through an introducer catheter 302 to provide access for the trigger wire arrangement 319 to the secondary stent graft 315. The trigger wire arrangement 319 may also be disposed through an auxiliary catheter (not shown). The trigger wire arrangement 319 is configured to retain the proximal 337 and distal ends 339 of the secondary stent graft 315 when the secondary stent graft 315 is in the compressed position. The proximal 337 and distal ends 339 may includes suture arrangements which contain one or more loops configured to engage with the trigger wire arrangement 319 (as described in FIG. 7). With the secondary stent graft 315 in the compressed position, an increased amount of working area is provided within the lumen of the longer leg 348 for the deployment of other endoluminal devices through the access port 336. In addition, an operator would have unrestricted access to the internal artery through the access port 336 while the secondary stent graft 315 is restrained the compressed position.

The trigger wire arrangement 319 may be used with a delivery device, such as that described in PCT application WO98/53761, entitled "A Prosthesis and a Method and Means of Deploying a Prosthesis," which is incorporated herein by reference in its entirety, used to deploy the endoluminal prosthesis assembly 301. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath.

Figure 11:
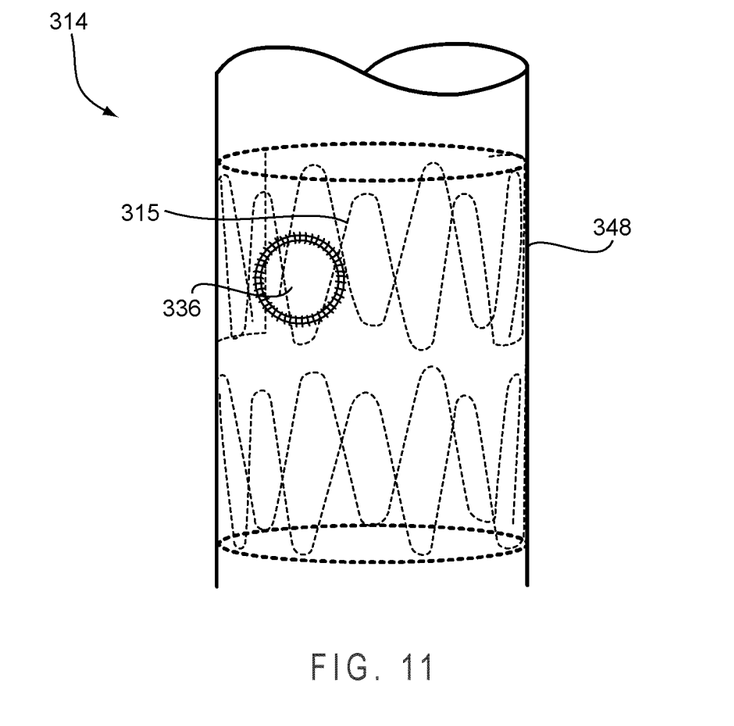
FIG. 11 shows a cross-sectional view of the secondary stent graft of the endoluminal prosthesis assembly of FIG. 9, where a secondary stent graft is in an expanded position.

FIG. 11 discloses an embodiment of the long leg 348 of the primary stent graft 314 where the secondary stent graft 315 is in the expanded position. In the expanded position, the secondary stent graft 315 engages against the interior wall of the endoluminal prosthesis to effectively seal the access port 336. The secondary stent graft 315 is completely concentric with the primary stent graft 314. The sealing of the access port 336 precludes access to the internal artery and prevents the possibility of leaks into the prosthesis. The secondary stent graft 315 in the expanded position has an expanded diameter that is less than the expanded diameter of the long leg 348 in the expanded position. The secondary stent graft 315 is this embodiment has a length that is shorter than the length of the long leg 348. In alternative embodiments, the secondary stent graft 315 may have a length that is longer that the length of the longer leg 348.

In use, a guide wire for an introducer into the femoral artery, via an incision and extended up beyond the aortic bifurcation to the aorta. The operator deploys the introducer over the guide wire and positioned within the aorta of a patient. The main body 323, the short leg 346 and the long leg 348 of the stent graft 314 are deployed, while retaining the superenal stent 331 on the proximal end 321 of the stent graft 314. The secondary stent graft 315, disposed within the interior of the long leg 348 in the compressed position, is retained by trigger wire arrangement 319. The trigger wire arrangement 319 engages the suture arrangements secured on the proximal 337 and distal ends 339 of the secondary stent graft 315. The operator introduces a catheter into the long leg through the side arm 358 and into the lumen of the long leg 348. Through the catheter, the operator can introduce additional endoluminal devices, including, but not limited to, a branch stent graft, into an internal artery through the access port 336. The secondary stent graft 315 in the compressed position provides the operator with access to the access port 336. Following deployment of the additional endoluminal prosthesis through the access port 336, the catheter is removed. The operator may remove the trigger wire arrangement 319 restraining the proximal 337 and distal 339 ends of the secondary stent graft 315. The secondary stent graft 315 moves from the compressed position to the expanded position. The secondary stent graft 315 in the expanded position is concentric with the long leg 348, and engages the walls to effectively seal the access port 336. The operator then releases the suprarenal stent 331 on the proximal end 321 of the primary stent graft 314, and the delivery device is removed from the patient.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. An endoluminal prosthesis assembly comprising:
a first stent graft comprising a biocompatible graft material and having a first end and a second end and an interior lumen, the first stent graft having an expanded position and a compressed position, the first stent graft defining an access port disposed through a wall of the first stent graft between the first end and the second end of the first stent graft; and
a second stent graft comprising a biocompatible graft material and having a first end and a second end and a lumen disposed therethrough, the second stent graft disposed within the interior lumen of the first stent graft, the second stent graft having an expanded position and a compressed position where the second stent graft in the compressed position is compressed against an interior wall of the interior lumen of the first stent graft positioned opposite the wall comprising the access port, and wherein the second stent graft in the compressed position is positioned diametrically opposite to the wall comprising the access port;
where when the first stent graft is in the expanded position and the second stent graft is in the compressed position, the second stent graft contacts only a portion of the interior wall of the interior lumen of the first stent graft and the access port is in fluid communication with the interior lumen of the first stent graft, and where when the first stent graft is in the expanded position and the second stent graft is in the expanded position, the second stent graft engages substantially all of the interior wall of the first stent graft and seals the access port from fluid communication with the interior lumen of the first stent graft.

2. The endoluminal prosthesis assembly of claim 1, where a portion of the second stent graft is secured to the interior wall of the first stent graft.

3. The endoluminal prosthesis assembly of claim 1, where the first stent graft has a length and the second stent graft has a length shorter than the length of the first stent graft.

4. The endoluminal prosthesis assembly of claim 1, where the first stent graft has a length and the second stent graft has a length longer than the length of the first stent graft.

5. The endoluminal prosthesis assembly of claim 1, where the second stent graft is restrained in the compressed position by a trigger wire arrangement.

6. The endoluminal prosthesis assembly of claim 5, where the trigger wire arrangement engages the first end of the second stent graft and the second end of the second stent graft.

7. The endoluminal prosthesis assembly of claim 5, where the trigger wire arrangement engages a first suture arrangement on the first end of the second stent graft.

8. The endoluminal prosthesis assembly of claim 7, where the trigger wire arrangement engages a second suture arrangement of the second end of the second stent graft.

9. The endoluminal prosthesis assembly of claim 1, where the second stent graft is concentric with the first stent graft and has a diameter in the expanded position that is less than the first stent graft in the expanded position.

10. An endoluminal prosthesis assembly comprising:
    a first stent graft comprising a biocompatible graft material and having a first end and a second end and an interior lumen, the first stent graft having an expanded position and a compressed position, the first stent graft defining an access port disposed through a wall of the first stent graft between the first and second ends of the first stent graft; and
    a second stent graft comprising a biocompatible graft material and having a first end and a second end and a lumen disposed therethrough, the second stent graft disposed entirely within the interior lumen of the first stent graft, the second stent graft having an expanded position and a compressed position where the second stent graft in the compressed position is compressed against an interior wall of the interior lumen of the first stent graft positioned opposite the wall comprising the access port, and wherein the second stent graft in the compressed position is positioned diametrically opposite to the wall comprising the access port;
    where when the first stent graft is in the expanded position and the second stent graft is in the compressed position, the first end and the second end of the second stent graft are restrained and the access port is in fluid communication with the interior lumen of the first stent graft, and where when the first stent is in the expanded position and the second stent graft is in the expanded position, the second stent graft engages substantially all of the interior wall of the first stent graft and seals the access port from fluid communication with the interior lumen of the first stent graft.

11. The endoluminal prosthesis assembly of claim 10, where the first end and the second end of the second stent graft are restrained in the compressed position by a trigger wire arrangement.

12. The endoluminal prosthesis assembly of claim 11, where the trigger wire arrangement engages a first suture arrangement on the first end of the second stent graft.

13. The endoluminal prosthesis assembly of claim 12, where the trigger wire arrangement engages a second suture arrangement of the second end of the second stent graft.

14. The endoluminal prosthesis assembly of claim 10, where the second stent graft is concentric with the first stent graft and has a diameter in the expanded position that is less than the first stent graft in the expanded position.

15. The endoluminal prosthesis assembly of claim 10, where the first stent graft has a length and the second stent graft has a length shorter than the length of the first stent graft.

16. A delivery system for an endoluminal prosthesis, comprising
    an introducer, the introducer having a distal end configured to remain outside a patient in use and a proximal end,
    a carrier for an endoluminal prosthesis assembly disposed within the introducer, the endoluminal prosthesis assembly comprising,
    a first stent graft comprising a biocompatible graft material and having a first end and a second end and an interior lumen, the first stent graft having an expanded position and a compressed position, the first stent graft defining an access port disposed through a wall of the first stent graft between the first and second ends of the first stent graft; and
    a second stent graft comprising a biocompatible graft material and having a first end and a second end and a lumen disposed therethrough, the second stent graft being disposed within the first stent graft, the second stent graft having an expanded position and a compressed position where the second stent graft in the compressed position is compressed against an interior wall of the interior lumen of the first stent graft positioned opposite the wall comprising the access port, and wherein the second stent graft in the compressed position is positioned diametrically opposite to the wall comprising the access port; and
    a trigger wire arrangement at least partially disposed through the lumen of the second stent graft and engaging the first end and the second end of the second stent graft to restrain the second stent graft in the compressed position.

17. The delivery system of claim 16, where the trigger wire arrangement comprises one or more wires.

18. The delivery system of claim 16, where the first end and the second end of the second stent graft include suture arrangements.

19. The delivery system of claim 18, where the suture arrangements include a plurality of loops to engage the trigger wire arrangement.

20. The delivery system of claim 16, where the trigger wire arrangement is substantially disposed through an auxiliary catheter.

* * * * *